US006962155B1

(12) United States Patent
Sinderby (10) Patent No.: US 6,962,155 B1
(45) Date of Patent: Nov. 8, 2005

(54) TARGET DRIVE VENTILATION GAIN CONTROLLER AND METHOD

(75) Inventor: Christer Sinderby, Montreal (CA)

(73) Assignee: Universite de Montreal, Montreal (CA)

(*) Notice: Subject to any disclaimer, the term of this patent is extended or adjusted under 35 U.S.C. 154(b) by 0 days.

(21) Appl. No.: 09/364,592

(22) Filed: Jul. 30, 1999

(51) Int. Cl.$^7$ ............................................. A61M 16/00
(52) U.S. Cl. ........................... 128/204.23; 128/204.21; 128/204.18
(58) Field of Search ...................... 128/204.18, 204.21, 128/204.23

(56) References Cited

U.S. PATENT DOCUMENTS

| | | | | |
|---|---|---|---|---|
| 3,923,055 A | * | 12/1975 | Hammacher | 128/204.21 |
| 4,256,100 A | * | 3/1981 | Levy et al. | 128/204.21 |
| 4,648,365 A | * | 3/1987 | Bostelman | 128/204.23 |
| 4,889,116 A | * | 12/1989 | Taube | 128/204.23 |
| 5,038,773 A | * | 8/1991 | Norlien et al. | 128/205.23 |
| 5,174,287 A | * | 12/1992 | Kallok et al. | 128/200.24 |
| 5,183,038 A | * | 2/1993 | Hoffman et al. | 128/204.21 |
| 5,188,098 A | * | 2/1993 | Hoffman et al. | 128/204.23 |
| 5,271,389 A | * | 12/1993 | Isaza et al. | 128/204.21 |
| 5,316,009 A | * | 5/1994 | Yamada | 128/204.21 |
| 5,319,540 A | * | 6/1994 | Isaza et al. | 364/161 |
| 5,353,788 A | * | 10/1994 | Miles | 128/204.23 |
| 5,365,922 A | * | 11/1994 | Raemer | 128/204.23 |
| 5,373,842 A | * | 12/1994 | Olsson et al. | 128/204.21 |
| 5,524,632 A | * | 6/1996 | Stein et al. | 607/20 |
| 5,542,415 A | * | 8/1996 | Brody | 128/204.23 |

(Continued)

FOREIGN PATENT DOCUMENTS

| | | |
|---|---|---|
| FR | 2 596 279 | 10/1987 |
| WO | WO 97/22377 | 6/1997 |

OTHER PUBLICATIONS

Iotti et al., "Closed-loop control of airway occlusion pressure at 0.1 second ($P_{0.1}$) applied to pressure-support ventilation: Algorithm and application in intubated patients," *Crit. Care Med.*, vol. 24, No. 5, p. 771 (1996).

Hayt, Jr. and Hughes, *Introduction to electrical engineering*, McGraw-Hill, New York: 162-163, 1968.

*Primary Examiner*—Mital Patel
(74) *Attorney, Agent, or Firm*—Fulbright & Jaworski, LLP (57) ABSTRACT

A gain controller and method for controlling the value of a gain is used in conjunction with an electrode array for detecting a signal representative of respiratory drive output of a patient during inspiration, and a lung ventilator for assisting inspiration of the patient. The gain controller comprises an input for receiving the signal representative of respiratory drive output; a comparator for determining whether the signal representative of respiratory drive output is higher or lower than a target drive signal; and a gain adjustment unit for increasing the value of a gain when the amplitude of the signal representative of respiratory drive output is higher than the amplitude of the target drive signal and for decreasing the value of this gain when the amplitude of the signal representative of respiratory drive output is lower than the amplitude of the target drive signal. The gain is applied to the signal representative of respiratory drive output to produce an amplified respiratory drive output representative signal used for controlling the lung ventilator. The advantage of target drive ventilation is that this mode of ventilation does not depend on pressure, flow or volume measurements. A leaky ventilatory line will introduce a change in respiratory drive which will change the ventilatory assist in order to return the respiratory drive to its target level. Also, changes in the patient's metabolic or pathophysiological status which result in altered respiratory drive will be compensated.

26 Claims, 11 Drawing Sheets

U.S. PATENT DOCUMENTS

| | | | |
|---|---|---|---|
| 5,671,752 A | 9/1997 | Sinderby et al. | 128/733 |
| 5,794,615 A | 8/1998 | Estes | 128/204.23 |
| 5,800,470 A * | 9/1998 | Stein et al. | 607/20 |
| 5,820,560 A | 10/1998 | Sinderby et al. | 600/600 |
| 5,857,459 A * | 1/1999 | Snow et al. | 128/204.21 |
| 5,890,490 A | 4/1999 | Aylsworth et al. | 128/203.12 |
| 5,937,854 A * | 8/1999 | Stenzler | 128/204.23 |
| 6,259,938 B1 * | 7/2001 | Zarychta et al. | 600/380 |
| 6,411,843 B1 * | 6/2002 | Zarychta | 600/546 |
| 6,584,347 B1 | 6/2003 | Sinderby | 600/546 |
| 6,588,423 B1 * | 7/2003 | Sinderby | 128/204.23 |
| 2003/0188748 A1 | 10/2003 | Sinderby et al. | 128/204.21 |
| 2003/0226565 A1 | 12/2003 | Sinderby et al. | 128/207.14 |

* cited by examiner

TARGET DRIVE VENTILATION GAIN CONTROLLER AND METHOD

BACKGROUND OF THE INVENTION

1. Field of the Invention

The invention relates to a target driven inspiratory assist ventilation system.

2. Brief Description of the Prior Art

The physiological mechanisms which generate myoelectrical activity when a muscle contracts have been known and understood for a long time. In particular, how to record signals from the muscles is one of the most extensively, theoretically described topics in physiology. Although the theoretical understanding is impressive, the bio-physiological application of these theories is, in practice, still deficient. As an example, no standardized analysis procedure has been developed for recording signals produced by activation of several, different motor units, the so called interference wave pattern. The interference wave pattern signal (EMG signal) contains an immense quantity of bio-physiological information about the given neuro-muscular function. However, as this EMG signal is very low in amplitude, it is sensitive to numerous artifacts. The influence of these artifacts varies in relation to the configuration of recording electrodes, the digitizing rate of the signal, and the type of recording technique.

Prior art analysis of interference wave pattern signals usually comprises a time consuming, tedious manual determination of the quality of the signal through visual inspection of this signal in the time domain. This determination is performed by a "subjective" investigator. Most of the prior art references describe how to calculate comparison estimates, but present very few comments on the signal quality. It is therefore not surprising to find that, in this technical field, independent studies evaluating the same questions have lead to different or even contradictory results.

Also in the prior art, the patient's inspiratory flow and volume has been used to control inspiratory proportional pressure assist ventilation. Proper adjustment of the relative contribution of flow and volume support during the inspiration requires knowledge of the elastic and viscous properties of the patient's respiratory system. Since the elastic and viscous properties may change, these measurements must be repeated at regular intervals. Correct and repeated measurements of elastance and resistance are difficult to set up in an intensive care unit. Moreover, in the presence of intrinsic positive end-expiratory pressure, the flow-volume controlled proportional assist ventilation may fail to trigger during whole breaths, and will definitively fail to trigger during at least the initial part of the inspiration which precedes the onset of flow; this period can last up to 300 ms in the case of a patient suffering from obstructive pulmonary disease. Finally leakage in the system will influence and may disturb the performance of the flow controlled proportional assist ventilation.

Traditionally, the goal of mechanical ventilation has been to maintain an optimal minute ventilation and respiratory load, and therefore, has included specific measurements of inspiratory flow and tidal volume. New concepts in mechanical ventilation allow patients to take over the control of ventilatory support delivered, both in terms of magnitude and duration. New technology has also incorporated new methods of applying ventilatory assist for example, mask ventilation, uncuffed endotracheal tubes, and miniature endotracheal tubes. These devices frequently cause leakage of gases such that measurement of flow and volume become erroneous.

Current technology is therefore often limited in its ability to detect and correct for these gas leaks and patients are at risk of becoming hyper- or hypo-ventilated.

OBJECTS OF THE INVENTION

An object of the present invention is therefore to overcome the above described drawbacks of the prior art.

Another object of the present invention is to provide a method and a device capable of adjusting the degree of inspiratory assist in relation to the real need of the patient, i.e. only to compensate for the degree of incapacity of the patient.

A further object of the present invention is to provide a method and a device for controlling inspiratory proportional pressure assist ventilation which requires no knowledge of the elastic and viscous properties of the patient's respiratory system, is not influenced by intrinsic positive end-expiratory pressure, altered muscle function, and is not influenced by air leakage of the lung ventilator unless the leakage exceeds the pumping capacity of the ventilator.

SUMMARY OF THE INVENTION

More specifically, in a preferred embodiment of the invention, there is provided a gain controller for adjusting, in relation to a target drive signal, the value of a gain applied to a signal representative of respiratory drive output of a patient during inspiration, to produce an amplified respiratory drive output representative signal for controlling a lung ventilator assisting inspiration of the patient. The gain controller comprises:

a first input for receiving the signal representative of respiratory drive output having a first amplitude;

a second input for receiving the target drive signal of a second amplitude;

a comparator for determining whether the amplitude of the signal representative of respiratory drive output is higher or lower than the amplitude of the target drive signal; and a gain adjustment unit for increasing the value of the gain when the amplitude of the signal representative of respiratory drive output is higher than the amplitude the target drive signal and for decreasing the value of the gain when the amplitude of the signal representative of respiratory drive output is lower than the amplitude of the target drive signal.

In another embodiment of the invention, there is provided a method for adjusting, in relation to a target drive signal, the value of a gain applied to a signal representative of respiratory drive output of a patient during inspiration, to produce an amplified respiratory drive output representative signal for controlling a lung ventilator assisting inspiration of the patient. The method comprises:

receiving the signal representative of respiratory drive output having a first amplitude;

receiving the target drive signal of a second amplitude;

determining whether the amplitude of the signal representative of respiratory drive output is higher or lower than the amplitude of the target drive signal; and increasing the value of the gain when the amplitude of the signal representative of respiratory drive output is higher than the amplitude of said target drive signal; and decreasing the value of the gain when the amplitude of the signal representative of respiratory drive output is lower than the amplitude of the target drive signal.

Target drive ventilation is based on the assumption that the patient's respiratory centers are intact and the patient is able to control minute ventilation as long as he/she has sufficient respiratory muscle. In a preferred embodiment of the invention, determination of respiratory drive is made by measuring the electrical activation of the diaphragm during an inspiration. Of course, any other signal representative of respiratory drive output may be used in other embodiments of the invention. Electrical activity of the diaphragm has previously been demonstrated to reflect global respiratory drive. The inspiratory electrical activation of the diaphragm can be quantified as the mean, median, total, peak, etc. and the trend of the previous breaths is used to adjust ventilatory assist for the present breath.

The invention is aimed to control ventilatory assist levels in order to maintain the respiratory drive (determined by diaphragm electric activation) at a sustainable target level. The lung ventilator can use a pressure/flow/volume generating device with a control unit which operates to maintain the mean (could also be median/peak/total, etc.) pressure/flow/volume in the ventilatory line sufficient for maintaining a constant target diaphragm electrical activity. The diaphragm electrical activity during a breath will be calculated in order to determine the mean (could also be median/peak/total, etc.) neural drive to the diaphragm for that particular breath. The trend for respiratory drive can be obtained from diaphragm electrical activity of previous breaths such that one can determine whether respiratory drive increases, decreases, or remains constant. A trend for a change in diaphragm electrical activity indicating an increase in respiratory drive will result in a progressive increase ventilatory assist until diaphragm electrical activity, i.e., respiratory drive has returned to its target level. Similarly, the decrease in diaphragm electrical activity, indicating reduced respiratory drive, will produce a progressive decrease in ventilatory assist until diaphragm electrical activity i.e. respiratory drive has returned to its target level.

Target Drive Ventilation would be more efficiently used in combination with Neurally Adjusted Proportional Pressure Assist (U.S. Pat. No. 5,820,560 to Sinderby et al., 1998), where ventilatory assistance will be proportional to the patient's respiratory drive throughout the breath and the average respiratory drive would remain constant over time. For proportional assist ventilation or other modes which deliver varying levels of support, the increasing or decreasing levels of mean/total ventilatory assist will be adjusted by increasing or decreasing the gain factor applied in the respective functions.

Target drive ventilation can also be applied with other modes of ventilatory assist. For use with ventilatory support modes that provide constant levels of support, for example pressure support, the increasing or decreasing levels of mean/total ventilatory assist will be achieved by relative increases or decreases of the pressure support, the increasing or decreasing levels of mean/total ventilatory assist will be achieved by relative increases or decreases of the pressure support level. Extreme pressure support levels will be avoided by introducing safety limits.

The advantage of Target drive ventilation is that this mode of ventilation does not depend on flow or volume measurements. A leaky ventilatory line will introduce a change in respiratory drive which will change the ventilatory assist in order to return the respiratory drive to its target level. Also, changes in the patient's metabolic or patho-physiological status which result in altered respiratory drive will be compensated. In contrast with present methods of controlling mechanical ventilators, an increase in respiratory assistance using a signal representative of respiratory drive output (e.g., an EMG signal) does not affect the efficiency with which these signals reliably control the ventilator (unless of course the disease affects the neuro-muscular function).

A combination of Target Drive Ventilation and Neurally Adjusted Proportional Pressure Assist (U.S. Pat. No. 5,820,560), would provide partial correction for leaks within breaths and compensation for leaks over long periods of time. The use of neural triggers would also overcome issues related to intrinsic PEEP.

The objects, advantages and other features of the present invention will become more apparent upon reading of the following non restrictive description of a preferred embodiment thereof, given by way of example only with reference to the accompanying drawings.

DETAILED DESCRIPTION OF THE PREFERRED EMBODIMENT

Figure 1:
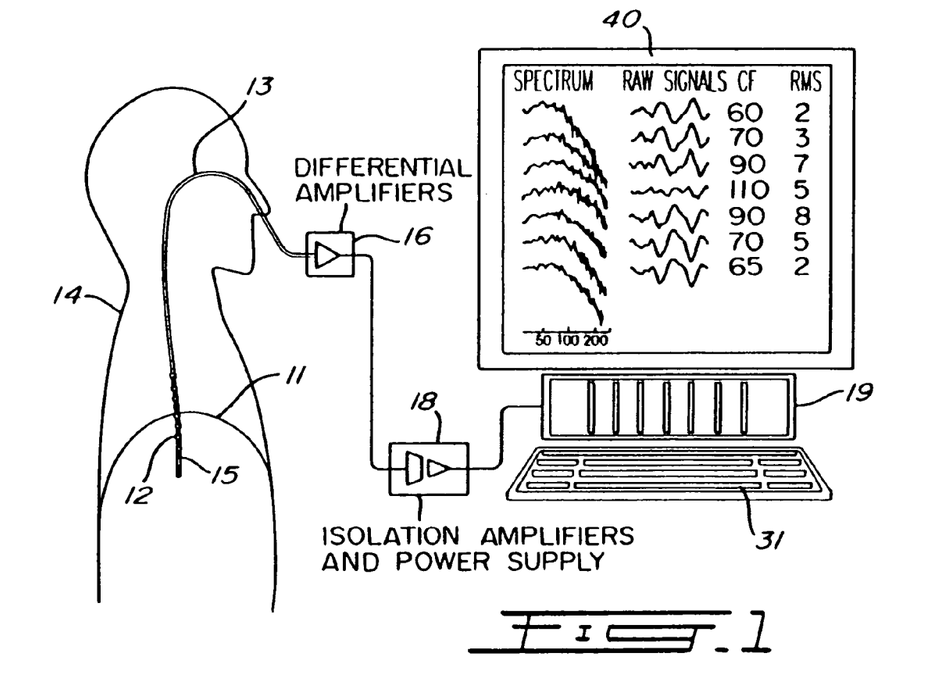
FIG. 1 is a schematic representation of a set-up of an EMG analysis system.
Figure 2:
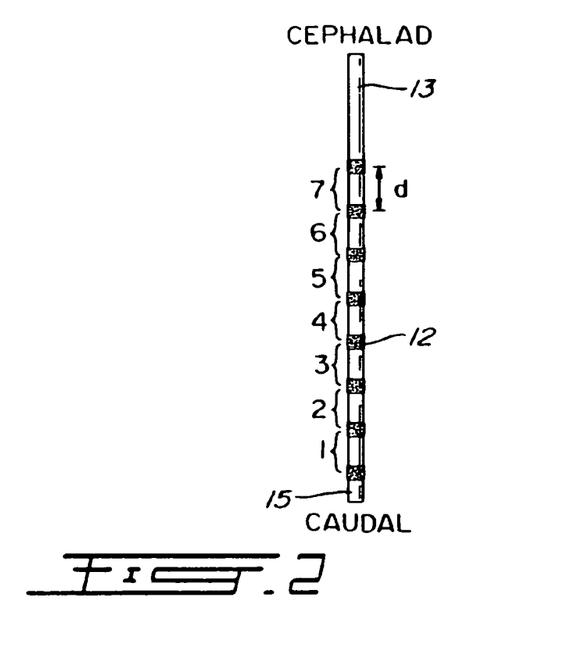
FIG. 2 is a section of oesophageal catheter on which an array of electrodes of the EMG analysis system of FIG. 1 is mounted.

To measure EMG activity of the diaphragm 11 (EMGdi) of a human patient 14, an array of electrodes such as 12 (FIGS. 1 and 2) are mounted on the free end section 15 of an oesophageal catheter 13, with a constant inter-electrode distance d (FIG. 2). As shown in FIG. 1, the catheter 13 is introduced into the patient's oesophagus through one nostril or the mouth until the array of electrodes 12 are situated at the level of the gastro esophageal junction. The diaphragm 11 and/or the oesophagus slightly move during breathing of the patient 14 whereby the array of electrodes 12 also slightly moves about the diaphragm 11. As will be explained in the following description, automatic compensation for this displacement is provided.

To mount an electrode 12 on the free end section 15 of the catheter 13, stainless steel wire (not shown) may be wound around the catheter 13. The wound stainless steel wire presents a rough surface smoothed out by solder, which in turn is electroplated with nickel, copper and then gold or silver. Of course, EMG signals from other muscles and other constructions of electrodes can be implemented.

Electric wires (not shown) interconnect each pair of successive electrodes such as 1–7 (FIG. 2) with a respective one of a group of differential amplifiers 16. This defines an overlap array. Obviously, these electric wires follow the catheter 13 from the respective electrodes 12 to the corresponding amplifiers 16, and are preferably integrated to the catheter 13. Preferably, the electric wires transmitting the EMGdi signals collected by the various pairs 1–7 of electrodes 12 are shielded to reduce the influence of external noise, in particular disturbance from the 50 or 60 Hz current and voltage of the electrical mains.

The group of differential amplifiers 16 amplifies (first subtraction step of the double subtraction technique) and band-pass filters each EMGdi signal. This first subtraction step may also be carried out in the personal computer 19 when the amplifiers 16 are single-ended or equivalently designed amplifiers (monopolar readings).

Figure 3:
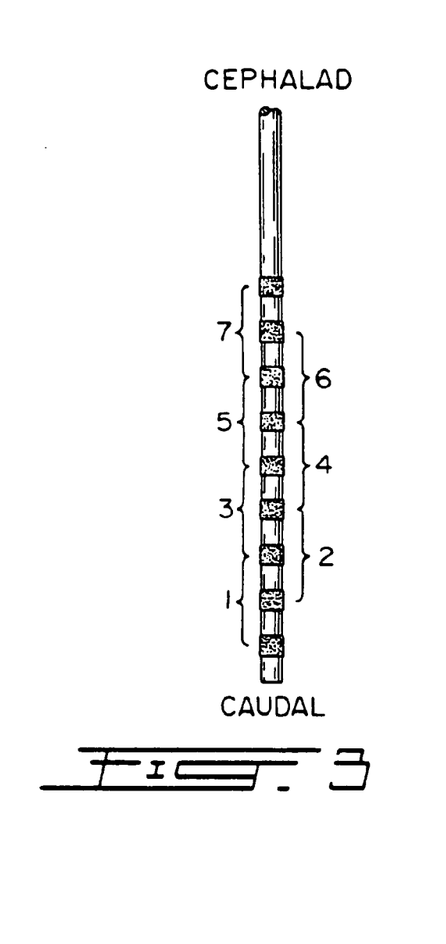
FIG. 3 illustrates a section of oesophageal catheter on which a second embodiment of the array of electrodes is mounted.

In the example illustrated in FIGS. 1 and 2, the free end section 15 of the catheter 13 is provided with an array of eight electrodes 12 defining seven pairs 1, 2, 3, 4, 5, 6 and 7 of successive electrodes 12 respectively collecting seven different EMGdi signals. Although it has been found that EMG activity of the diaphragm (EMGdi) can be measured accurately with an oesophageal catheter 13 provided on the free end section 15 thereof with an array of eight electrodes 12, a different number and/or configuration of pairs of electrodes 12 can be contemplated depending on the patient's anatomy and movement of the diaphragm. Also, the pairs 1–7 do not need to be pairs of successive electrodes; FIG. 3 illustrates an array of nine electrodes to form seven overlapping pairs of electrodes 1–7.

A major problem in recording EMGdi signals is to maintain the noise level as low and as constant as possible. Since the electric wires transmitting the EMGdi signals from the electrodes 12 to the differential amplifiers 16 act as an antenna, it is crucial, as indicated in the foregoing description, to shield these electric wires to thereby protect the EMGdi signals from additional artifactual noise. Also, the package enclosing the differential amplifiers 16 is preferably made as small as possible (miniaturized) and is positioned in close proximity to the patient's nose to decrease as much as possible the distance between the electrodes 12 and the amplifiers 16.

The amplified EMGdi signals are supplied to a personal computer 19 through respective isolation amplifiers of a unit 18. Unit 18 supplies electric power to the various electronic components of the differential and isolation amplifiers while ensuring adequate isolation of the patient's body from such power supply. The unit 18 also incorporates bandpass filters included in the respective EMGdi signal channels to eliminate the effects of aliasing. The EMGdi signals are then digitally processed into the personal computer 19 after analog-to-digital conversion thereof. This analog-to-digital conversion is conveniently carried out by an analog-to-digital converter implemented in the personal computer 19. The personal computer 19 includes a monitor 40 and a keyboard 31.

It is believed to be within the capacity of those of ordinary skill in the art to construct suitable differential amplifiers 16 and an adequate isolation amplifiers and power supply unit 18. Accordingly, the amplifiers 16 and the unit 18 will not be further described in the present specification.

Figure 4:
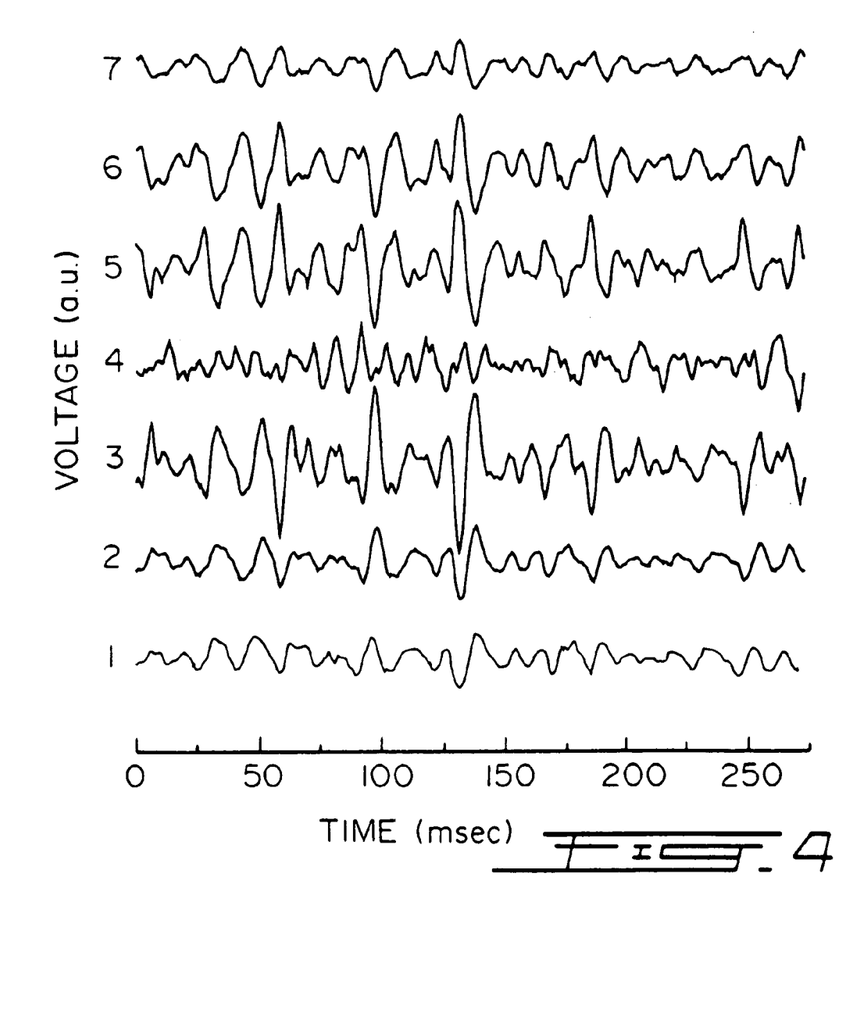
FIG. 4 is a graph showing a set of EMGdi signals of the diaphragm detected by pairs of successive electrodes of the array of FIG. 2.

An example of the seven EMGdi signals collected by the pairs 1–7 of successive electrodes 12 (FIGS. 1 and 2) and supplied to the computer 19 is illustrated in FIG. 4.

As the diaphragm is generally perpendicular to the longitudinal axis of the oesophageal catheter 13 equipped with an array of electrodes 12, only a portion of the electrodes 12 are situated in the vicinity of the diaphragm. It is therefore important to determine the position of the diaphragm with respect to the oesophageal electrode array.

The portion of the crural diaphragm 11 which forms the muscular tunnel through which the oesophageal catheter 13 is passed is referred to the "diaphragm depolarizing region" (DDR). The thickness of the DDR is 20–30 mm. It can be assumed that, within the DDR, the distribution of active muscle fibers has a center from which the majority of the EMGdi signals originate, i.e. the "diaphragm depolarizing region center" (DDR center). Therefore, EMGdi signals detected on opposite sides of the DDR center will be reversed in polarity with no phase shift; in other words, EMGdi signals obtained along the electrode array are reversing in polarity at the DDR center.

Moving centrally from the boundaries of the DDR, EMGdi power spectrums progressively attenuate and enhance in frequency. Reversal of signal polarity on either side of the electrode pair 4 with the most attenuated power spectrum confirms the position from which the EMGdi signals originate, the DDR center.

Figure 5A:
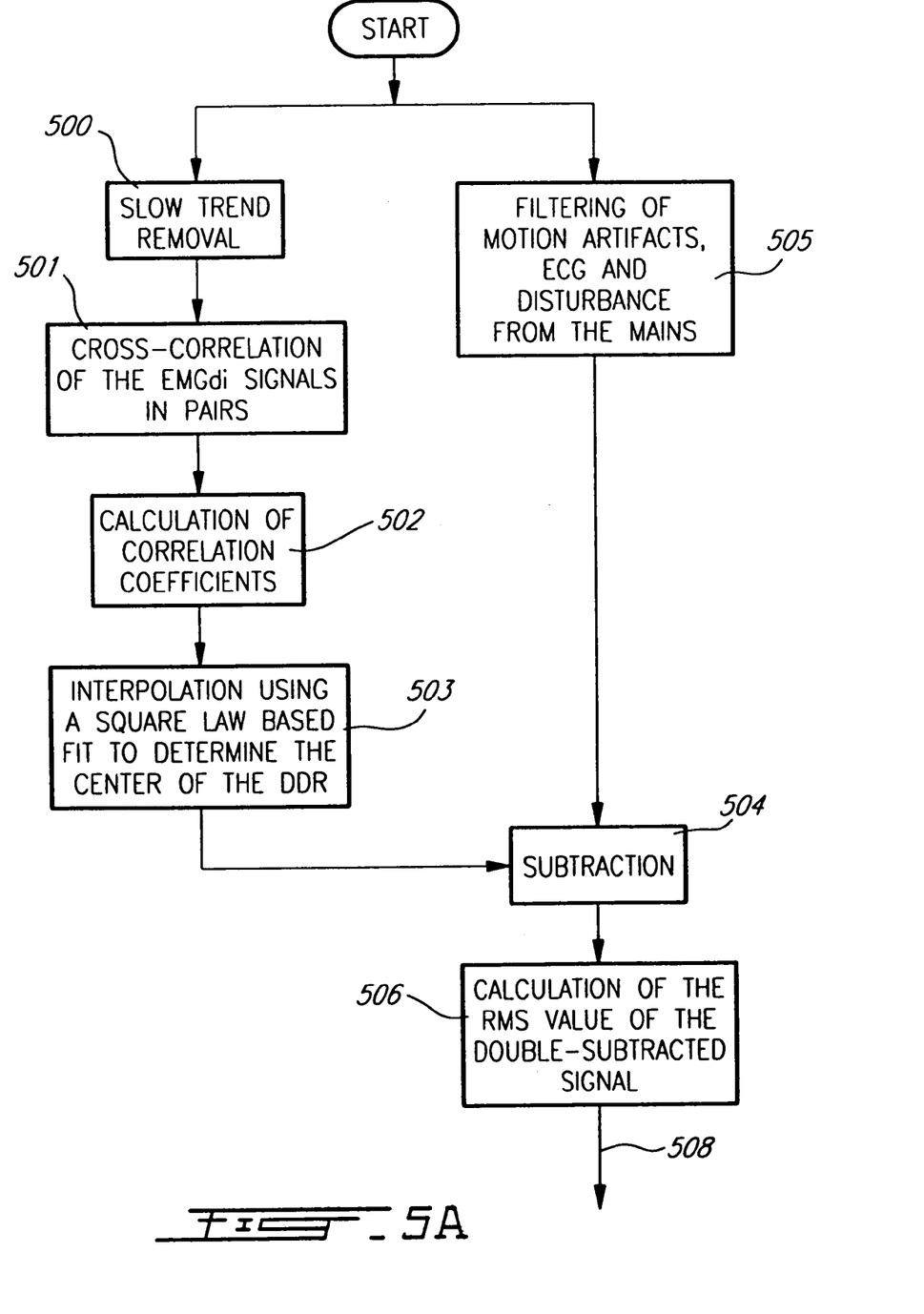
FIG. 5A is a flow chart showing a method for conducting double subtraction technique of the EMGdi signals.

Referring to FIG. 5A, the first task of the computer 19 is to determine the center of the DDR. The center of the DDR is repeatedly determined at predetermined time intervals.

For that purpose, slow trend is first removed from each EMGdi signal (step 500). To carry out such trend removal, the processing conducted by the computer 19 on each EMGdi signal is equivalent to high-pass filtering each EMGdi signal at a transition frequency of about 20 Hz. In particular, step 500 will remove the direct current component of the EMGdi signals to enable the computer 19 to evaluate the polarities of the EMGdi signals relative to each other.

In step 501, the EMGdi signals are cross-correlated in pairs. As well known to those of ordinary skill in the art, cross-correlation is a statistical determination of the phase relationship between two signals and essentially calculates the similarity between two signals in terms of a correlation coefficient r (step 502). A negative correlation coefficient r indicates that the cross-correlated signals are of opposite polarities.

Figure 6:
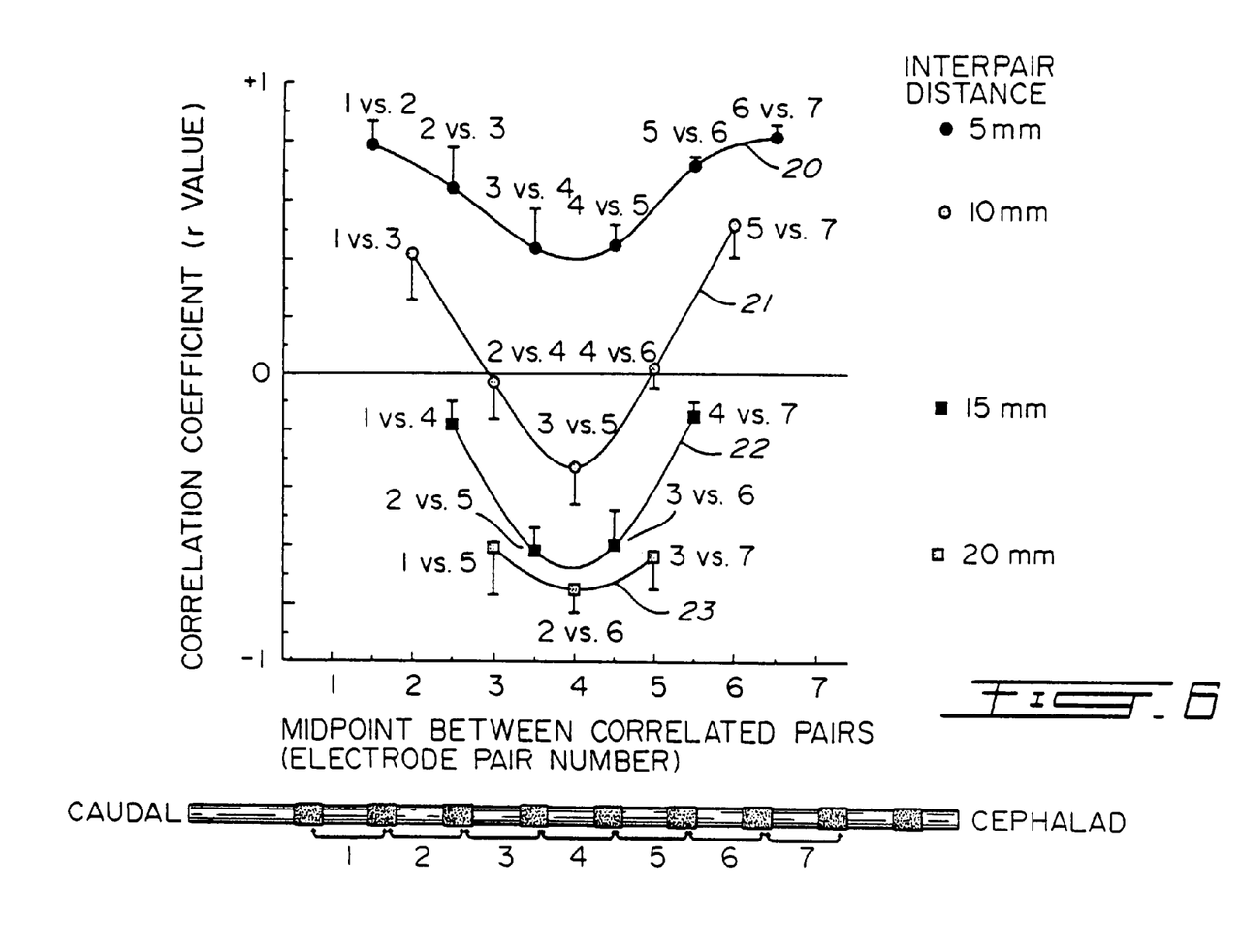
FIG. 6 is a graph showing the distribution of correlation coefficients calculated for determining the position of the center of the depolarizing region of the diaphragm along the array of electrodes of FIG. 2.

FIG. 6 shows curves of the value of the correlation coefficient r versus the midpoint between the pairs of electrodes from which the correlated EMGdi signals originate. In this example, the inter-electrode distance is 10 mm. Curves are drawn for distances between the correlated pairs of electrodes 12 of 5 mm (curve 20), 10 mm (curve 21), 15 mm (curve 22) and 20 mm (curve 23). One can appreciate from FIG. 5A that negative correlation coefficients r are obtained when EMGdi signals from respective electrode pairs situated on opposite sides of the electrode pair 4 are cross-correlated. It therefore appears that the change in polarity occur in the region of electrode pair 4, which is confirmed by the curves of FIG. 4. Accordingly, it can be assumed that the center of the DDR is situated substantially midway between the electrodes 12 forming pair 4.

For example, the center of the DDR can be precisely determined by interpolation (step 503 of FIG. 5A) using a square law based fit of the three most negative correlation coefficients of curve 21 obtained by successive cross-correlation of the EMGdi signals from each electrode pair to the EMGdi signals from the second next electrode pair. Association of the center of the DDR to a pair of electrodes 12 provides a "reference position" from which to obtain EMGdi signals within the DDR. Such control is essential in overcoming the artifactual influence on the EMGdi power spectrum.

It has been experimentally demonstrated that EMGdi signals recorded in the oesophagus are satisfactory as long as they are obtained from electrode pairs (with an inter-electrode distance situated between 5 and 20 mm) positioned at a distance situated between 5 and 30 mm on the opposite sides of the DDR center (the inter-pair distance being therefore situated between 5 and 30 mm). Although EMGdi signals obtained from these positions offers a clear improvement in acceptance rate, the signal-to-noise ratio during quiet breathing still tends to remain unsatisfactorily low.

In another embodiment of the invention, step 500 can be eliminated and steps 501, 502 and 503 could be implemented immediately after step 505.

Figure 7:
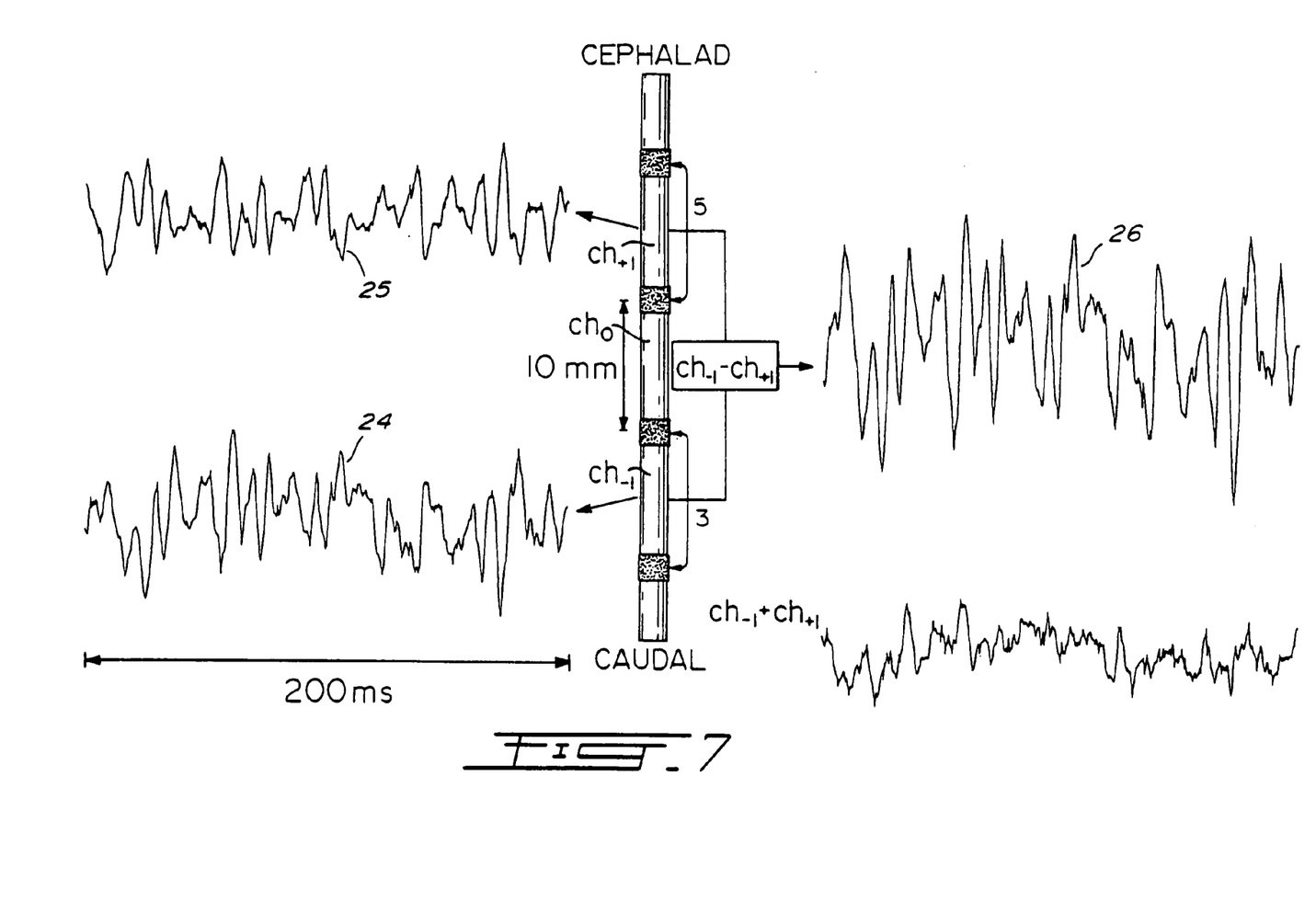
FIG. 7 is a schematic diagram illustrating in the time domain a double subtraction technique for improving the signal-to-noise ratio and to reduce an electrode-position-induced filter effect.

For example, in FIG. 4, the EMGdi signals originating from the electrode pairs 3 and 5 situated respectively 10 mm below and 10 mm above the DDR are strongly inversely correlated at zero time delay. In contrast to the inversely correlated EMGdi signals, the noise components for electrode pairs 3 and 5 are likely to be positively correlated. Hence, as illustrated in FIG. 7, subtraction of the EMGdi signals 24 and 25 from electrode pairs 3 and 5 will result into an addition of the corresponding EMGdi signals (signal 26 of FIG. 6) and into a subtraction, that is an elimination of the common noise components. This technique will be referred to as "the double subtraction technique" (step 504 of FIG. 5A).

Subtraction step 504 (second subtraction step of the double subtraction technique) can be carried out either in the time domain, or after conversion of signals 24 and 25 in the frequency domain. Double subtraction technique can be performed by subtracting other combinations of signals, for example by subtracting the EMGdi signal from electrode pair 2 from the EMGdi signal from electrode pair 5 (FIG. 4), by subtracting signal from electrode pair 6 from the signal from electrode pair 3 and by adding these differences, etc. Other means for reducing the effect of electrode filtering can be applied.

The double subtraction technique is carried out in step 504 on the pair of EMGdi signals (for example the signals from electrode pairs 3 and 5 shown in FIG. 4) identified in step 503, after appropriate filtering of these EMGdi signals in step 505. Filtering step 505 will remove from each EMGdi signal the motion artifacts, the electrocardiogram (ECG) component, and the disturbance from the electrical mains. Motion artifacts are induced by motion of the electrodes. More generally, motion artifacts are defined as a low frequency fluctuation of the EMGdi signals' DC level induced by mechanical alterations of the electrode metal to electrolyte interface i.e. changes in electrode contact area and/or changes in pressure that the tissue exerts on the electrode.

Figure 8A:
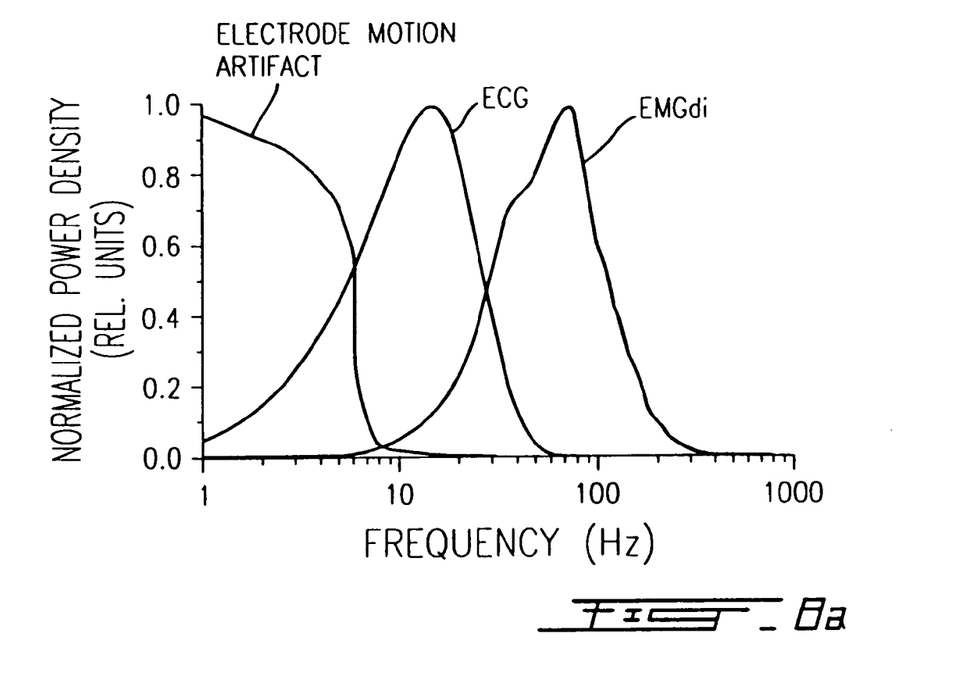
FIG. 8a is a graph showing the power density spectrum of electrode motion artifacts, the power density spectrum of ECG, and the power density spectrum of EMGdi signals.
Figure 8B:
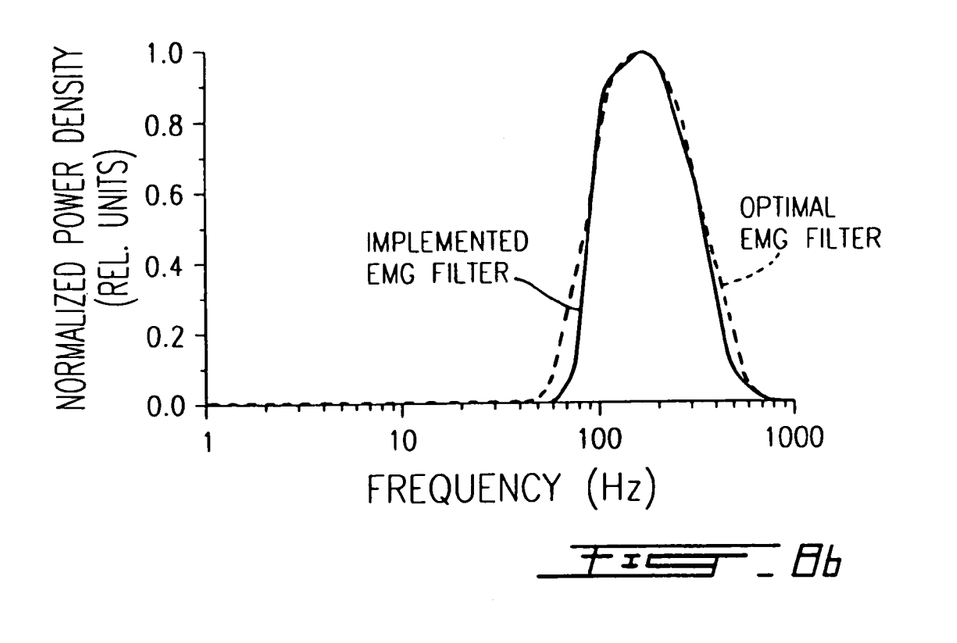
FIG. 8b is a graph showing an example of transfer function for a filter to be used for filtering out the electrode motion artifacts, ECG, and the 50 or 60 Hz disturbance from electrical mains.

The graph of FIG. 8a shows the power density spectrum of the above defined electrode motion artifacts, the power density spectrum of ECG, and the power density spectrum of EMGdi signals. The graph of FIG. 8b shows an example of transfer function for a filter (the dashed line showing the optimal transfer function, and the solid line the transfer function implemented by the inventors) to be used in step 505 for filtering out the electrode motion artifacts, ECG, and the 50 or 60 Hz disturbance from the electrical mains. Processing of the EMGdi signals by the computer 19 to follow as closely as possible the optimal transfer function of FIG. 8b will conduct adequately filtering step 505.

Referring back to FIG. 5A, step 506 calculates the RMS (Root-mean-square) value of the double-subtracted signal produced in step 504. The increase in amplitude obtained with the double subtraction technique is associated with a twofold increase in RMS values. RMS values obtained with the double subtraction technique are closely and linearly related to the original signals. The RMS value can be replaced by any other value representative of the strength of the double-subtracted signal, for example mean, median, peak or total signal amplitudes.

Figure 9:
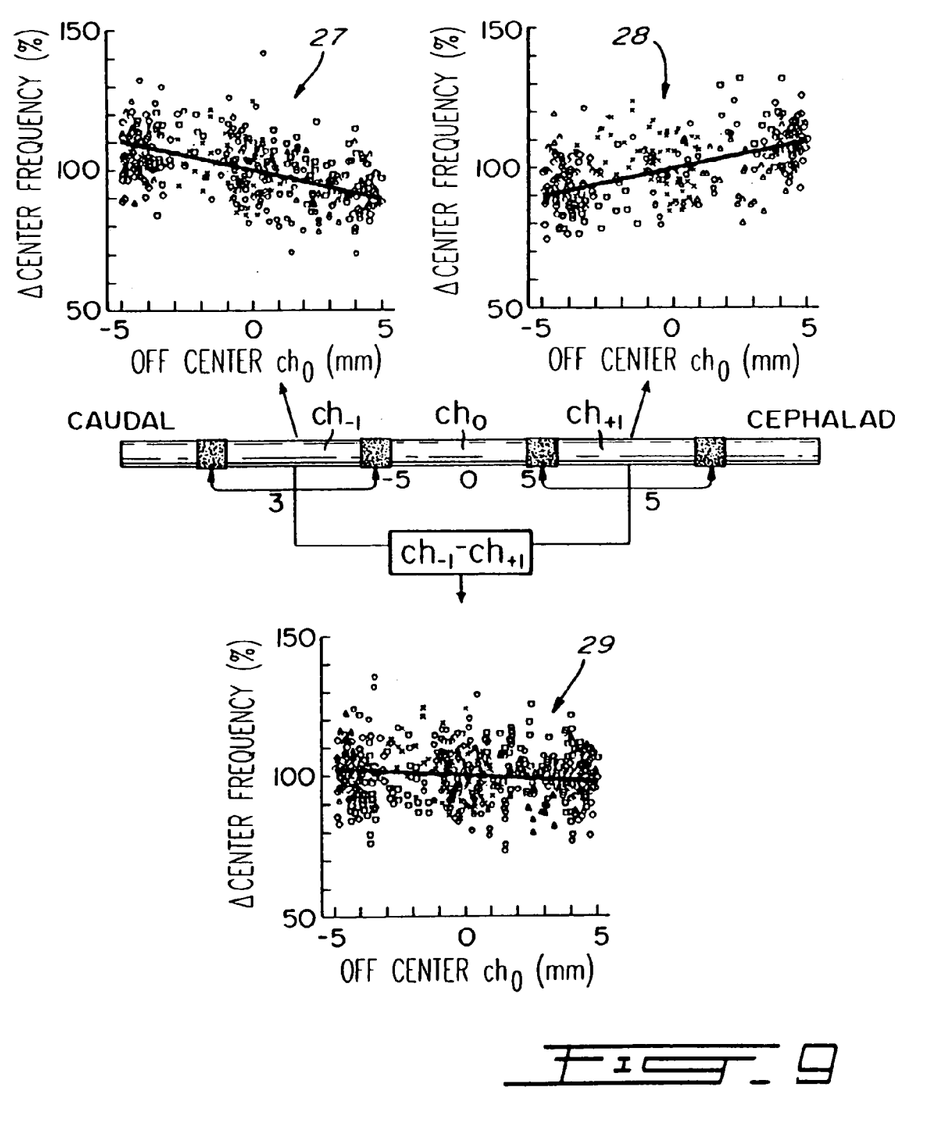
FIG. 9 is a schematic diagram illustrating in the frequency domain stabilization by the double subtraction technique of the center frequency upon displacement of the center of the depolarizing region of the diaphragm along the array of electrodes of FIG. 2.

The double subtraction technique compensates for the changes in signal strength and frequency caused by movement of the diaphragm 11 (FIG. 1) and/or the oesophagus during breathing of the patient 14 causing movement of the array of electrodes 12 with respect to the diaphragm 11. Referring to FIG. 9, off center of the array of electrodes 12 (electrode-position-induced filter effect) causes a variation of center frequency values (see curves 27 and 28) for the EMGdi signals from the electrode pairs 3 and 5. The double subtraction technique eliminates such variation of center frequency values as indicated by curve 29 as well as variation of signal strength. Therefore, the reciprocal influence of the position of the DDR center on the EMGdi signal frequency content is eliminated by the double subtraction technique.

It has been found that the double subtraction technique may improve the signal-to-noise ratio by more than 2 dB ratio and reduce an electrode-position-induced filter effect. Double subtraction technique is also responsible for a relative increase in acceptance rate by more than 30%.

Cross-talk signals from adjacent muscles are strongly correlated at zero time delay and equal in polarity between all pairs of electrodes 12. Hence, these cross-talk signals appear as a common mode signal for all electrode pairs and therefore, are eliminated by the double subtraction technique.

Figure 5B:
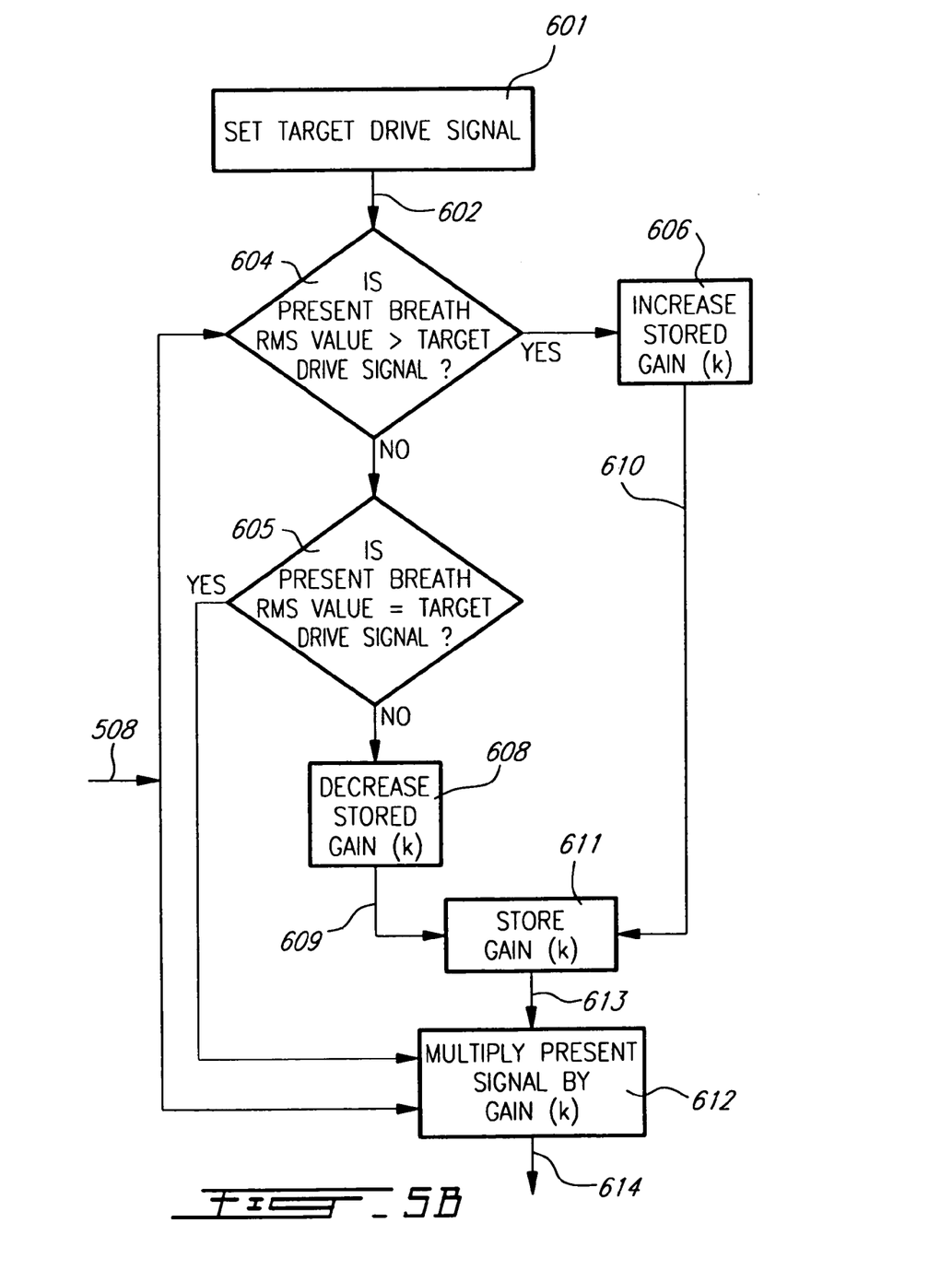
FIG. 5B is a flow chart showing a method for controlling a gain value in accordance with an embodiment of the invention.

Referring to FIG. 5B, a target drive signal is set by an operator at step 601. The output of block 601 is therefore the target drive signal 602. The value of the target drive signal 602 is determined by a person skilled in the art. The target drive signal 602 can be any signal which is representative of respiratory drive output. In a preferred embodiment of the invention, this signal can be any signal representative of the electrical activity of a muscle (i.e., electromyographic signal) that reflects the global respiratory drive. The target drive signal 602 can therefore be quantified, among others, the mean, the median, the total or the peak of the EMGdi signal. The target drive signal 602 is then compared to the RMS value on line 508 in block 604. If the present breath RMS value on line 508 is greater than the target drive signal 602, this indicates that there is a trend for a change in diaphragm electrical activity (EMGdi) indicating an increase in respiratory drive and requiring a progressive increase in ventilatory assistance. The result of the decision block 604 will be positive until the EMGdi 508 returns to the target level 602. In this case, the stored gain (k) will be increased in block 606. The gain (k) 610 will then be recorded in block 611 and outputted as signal 613.

Returning now to block 604, if the present breath RMS value on line 508 is not greater than the target drive signal 602, it may be equal or smaller. In block 605, it is determined if the present breath RMS value 508 is equal to the target drive signal 602. If it is equal, the gain value (k) does not change.

If the present breath RMS value 508 is not equal to the target drive signal 602, then it is smaller than the target drive signal 602, and this indicates a decrease in diaphragm electrical activity (EMGdi) resulting in reduced respiratory drive. It will therefore be necessary to progressively decrease the ventilatory assist until the diaphragm electrical activity (EMGdi) 508 returns to the target level 602. In this case, the result from decision block 604 will be negative resulting in a decrease in the stored gain (k) in block 608. The gain (k) 609 will then be stored at step 611 and outputted as signal 613.

Those skilled in the art will understand that the amount of the change (increase, step 606, or decrease, step 608) in ventilatory assistance is derived from experience, the patient's condition, the environment, etc. The amount of change can therefore be adjusted on a case by case basis. Also, in a particular embodiment of the invention, the increase or decrease in ventilatory assistance could be a relative value; that is, a fraction or percentage multiplied by, for example, the target drive signal, the signal representative of respiratory drive output, or a difference between the amplitude of the signal representative of respiratory drive output and the amplitude of the target drive signal.

Those skilled in the art will also understand that the test at steps 604 and 605 can include a certain range of amplitudes for the target drive signal 602 (whether they are absolute or relative amplitudes); that is, for example, the target drive signal could be X plus or minus a predetermined value. Therefore, at step 604, the present breath RMS value 508 needs to be greater than X plus the predetermined value in order to proceed to step 606. In the same way, at step 605, the present breath RMS value 508 needs to be smaller than X minus the predetermined value in order to proceed to step 608.

Finally, the present RMS value on line 508 will be multiplied by the gain (k) 613 in block 612 to produce a control signal 614. The control signal 614 will be the input to lung ventilator 54 of FIG. 10.

Figure 11:
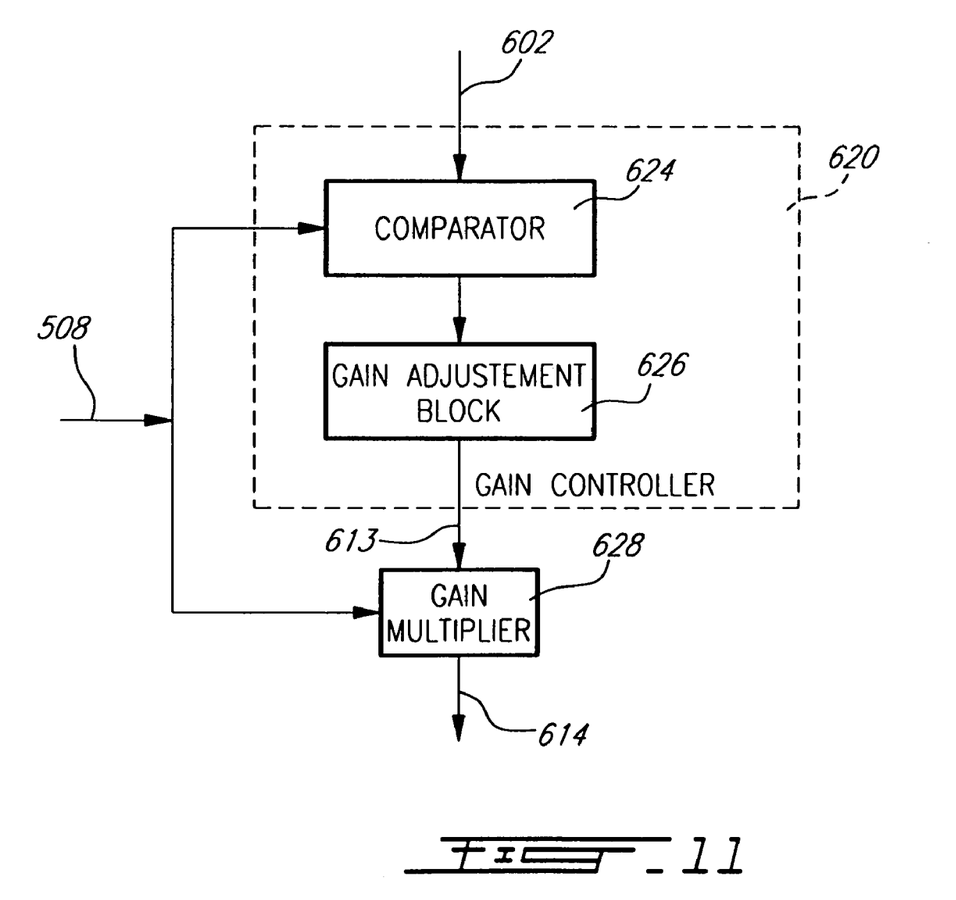
FIG. 11 is a schematic block diagram showing a structure for implementing the steps of the method described in FIG. 5B.

FIG. 11 illustrates a possible physical embodiment of steps 604, 605, 606, 608, 611, and 612 of FIG. 5B. A gain controller 620 and a gain multiplier 628 are provided. A first input to gain controller 620 is the RMS value on line 508, a second input to gain controller 620 is target drive signal 602, and the output of gain controller 620 is gain (k) 613 value. The gain (k) 613 value is then inputted to the gain multiplier 628 where it is multiplied by the RMS value on line 508 for the present inspiration (step 612 of FIG. 5B) resulting in a control signal 614.

The gain controller 620 further comprises a comparator 624 and a gain adjustment block 626. The comparator 624 implements steps 604 and 605 and the gain adjustment block 626 implements steps 606, 608 and 611 of FIG. 5B.

Figure 5C:
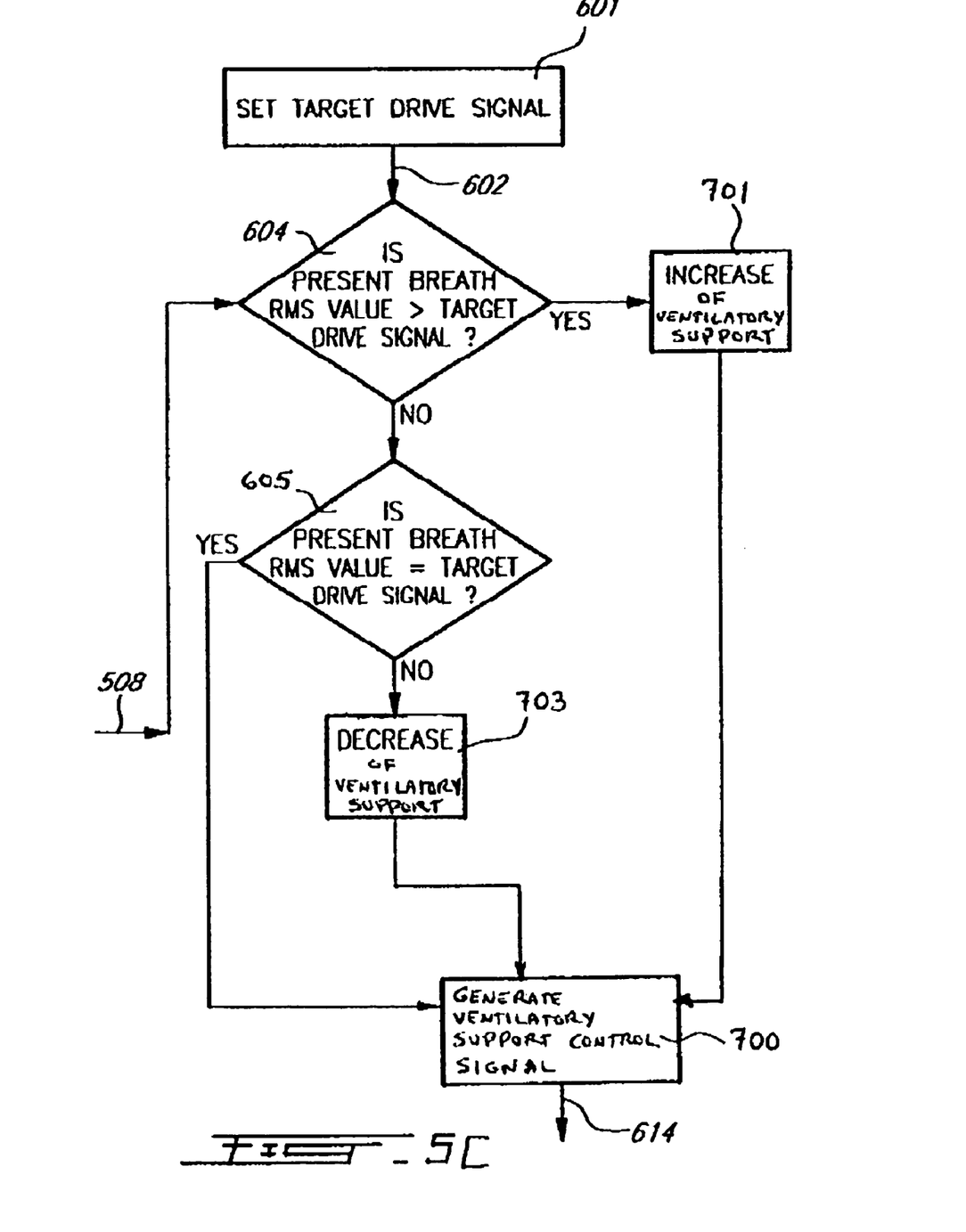
FIG. 5C is a flow chart showing an illustrative embodiment of a method according to the invention for controlling the level of a ventilatory support control signal for application to and control of a lung ventilator.

Referring to FIG. 5C, the target drive signal is set by an operator in block 601. The output of block 601 is therefore the target drive signal 602. The value of the target drive signal 602 is determined by a person skilled in the art. As indicated in the foregoing description, the target drive signal 602 can be any signal representative of respiratory drive output. In an illustrative embodiment, this signal can be any signal representative of the electrical activity of a muscle (i.e. electromyographic signal) that reflects the global respiratory drive. The target drive signal 602 can therefore be quantified as, among others, the mean, the median, the total or the peak of the EMGdi signal.

The target drive signal 602 is then compared to the RMS value on line 508 in block 604.

If the present breath RMS value on line 508 is greater than the target drive signal 602, this indicates that there is a trend for a change in diaphragm electrical activity (EMGdi) indicating an increase in respiratory drive and requiring an increase in ventilatory assistance. Block 701 then commands block 700 to produce an increase of the ventilatory support, for example pressure support, through an increase of the level of the ventilatory support control signal 614. The function of block 700 is to produce this ventilatory support control signal 614. In other words block 701 commands block 700 to increase the level of the ventilatory support control signal 614 by a given amount.

Returning to block 604, if the present breath RMS value on line 508 is not greater than the target drive signal 602, it may be equal or smaller. In block 605, it is determined if the present breath RMS value 508 is equal to the target drive signal 602.

If it is equal, block 605 commands block 700 to keep the level of the ventilatory support control signal 614 constant.

Detection by block 605 that the present breath RMS value 508 is smaller than the target drive signal 602 indicates a decrease in diaphragm electrical activity (EMGdi) resulting in reduced respiratory drive. Block 703 then commands block 700 to produce a decrease of the ventilatory support, for example pressure support, through a decrease of the level of the ventilatory support control signal 614. In other words block 703 commands block 700 to decrease the level of the ventilatory support control signal 614 by a given amount.

Those of ordinary skill in the art will understand that the amount of the change (increase or decrease) in ventilatory assistance is derived from experience, the patient's condition, the environment, etc. The amount of change can therefore be adjusted on a case by case basis.

Those of ordinary skill in the art will also understand that the test at blocks 604 and 605 can include a certain range of amplitudes for the target drive signal 602 (whether they are absolute or relative amplitudes); for example, the target drive signal could be X plus or minus a predetermined value. Therefore, at block 604, the present breath RMS value 508 needs to be greater than X plus the predetermined value in order to proceed to block 701. In the same way, at step 605, the present breath RMS value 508 needs to be smaller than X minus the predetermined value in order to proceed to step 703.

Figure 10:
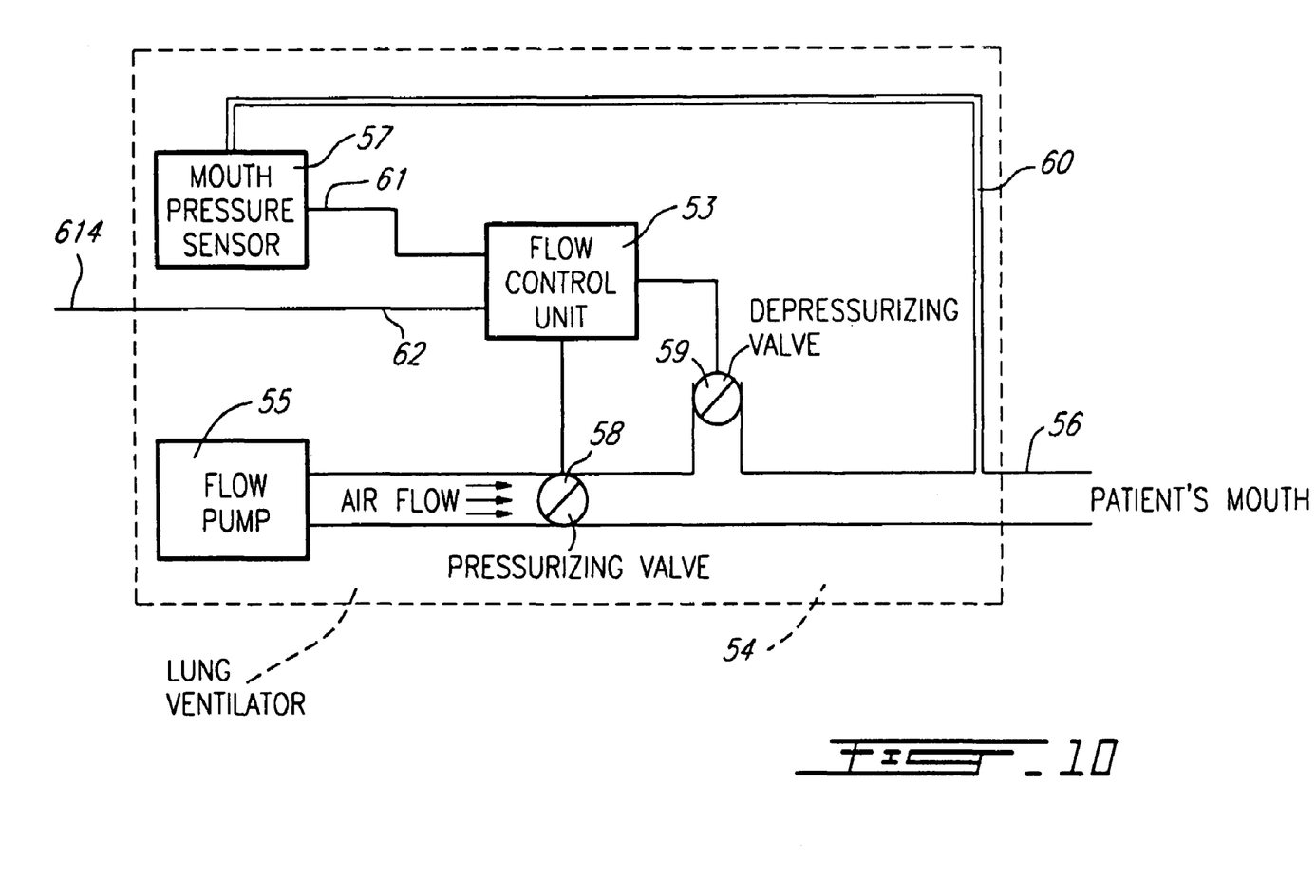
FIG. 10 is a schematic block diagram of a lung ventilator showing control of inspiratory proportional pressure assist ventilation by means of an EMG signal obtained with the above mentioned double subtraction technique.

FIG. 10 illustrates a lung ventilator 54 capable of being controlled by the multiplied, RMS value 614 of the double-subtracted signal produced in step 612 of FIG. 5B. Although an air-flow-based pressure ventilator is illustrated as an example in FIG. 10, it should be kept in mind that the RMS value of the double subtracted signal can be used for controlling any other lung ventilator.

Ventilator 54 shown in FIG. 10 as an illustrative example only comprises a flow control unit 53, a flow pump 55, a patient's respiratory (inspiratory and expiratory) implement 56 such as a mask, a tracheal tube connector, or any other respiratory implement, a pressure sensor 57, a pressurizing valve 58, and a depressurizing valve 59.

The flow pump 55 produces a constant air flow and supply of this air flow to the patient's respiratory accessory 56 is controlled through the pressurizing valve 58. The patient is allowed to breathe out through the respiratory accessory 56 and the depressurizing valve 59. The pressurizing and depressurizing valves 58 and 59 are controlled by the flow control unit 53.

The pressure sensor 57 is connected close to the respiratory implement 56 through a line 60. The pressure sensor 57 produces a corresponding respiratory pressure representative signal 61 supplied to the flow control unit 53. Accordingly, the pressure sensor 57 provides feedback of actual respiratory pressure close to the respiratory implement 56. The flow control unit 53 is also supplied with the multiplied, RMS value 614 of the double-subtracted signal delivered on line 62 (FIG. 10) by step 612 of FIG. 5B.

Those of ordinary skill in the art know that the amplitude of the multiplied, RMS value 614 of the double-subtracted signal delivered on line 62 is a representation of the demand to breathe from the brain.

When the RMS value 614 supplied to the flow control unit 53 is higher than the amplitude of the pressure representative signal 61, this indicates that the demand to breath from the brain is higher than the air actually breathed by the patient. Inspiratory assist is then required and the flow control unit 53 will open pressurizing valve 58 to supply air flow from the pump 55 to the patient's respiratory accessory (depressurizing valve 59 being closed) until the amplitude of the pressure representative signal 61 is equal to the multiplied, RMS value 614. The flow control unit 53 will continue to control the position of valve 58 to maintain the amplitude of the pressure representative signal 61 equal to the multiplied, RMS value 614 during all the inspiratory cycle.

During the inspiratory cycle, when the multiplied, RMS value 614 falls slightly below the amplitude of the pressure representative signal 61, depressurizing valve 59 can be opened to correct the situation and maintain the amplitude of the pressure representative signal 61 equal to the multiplied, RMS value 614.

When the multiplied, RMS value 614 drops below a given threshold, this indicates the beginning of an expiratory cycle. Then, the flow control unit 53 closes pressurizing valve 58 and opens depressurizing valve 59 to allow the patient to breath out through the respiratory accessory 56 and the depressurizing valve 59.

In another example embodiment of the invention, in order to obtain correct proportionality between the pressure representative signal 61 and the multiplied, RMS value 614, a gain adjustment is introduced for example in sensor 57 or on the line 62 to adequately control pressure assist to the respiratory implement 56 in function of the multiplied, RMS value 614.

Accordingly, the subject invention presents a major advantage over the prior art. Indeed, the degree of inspiratory assist is adjusted in relation to the real need of the patient. In other words, assist is proportional to the difference between the pressure representative signal 61 and the multiplied, RMS value 614. Inspiratory assist is therefore provided only to compensate for the degree of incapacity of the patient. The patient still contributes to inspiration as a function of his capacity to prevent the lung ventilator to further reduce the patient's inability to breathe. Requiring breathing efforts from the patient usually accelerates recovery of the patient and faster disconnection of the patient from the lung ventilator.

Although the present invention has been described herein above with reference to preferred embodiments thereof, these embodiments can be modified at will, within the scope of the appended claims, without departing from the spirit and nature of the subject invention.

What is claimed is:

1. A lung ventilator control system for maintaining at a sustainable target level a respiratory drive of a patient assisted by a lung ventilator during inspiration, comprising:
   a detector of the electrical activity of a muscle of the patient indicative of a respiratory drive of said patient, said detector producing a respiratory drive signal in response to the detected electrical activity;
   a target drive signal supply which, in operation, produces a target drive signal of given amplitude, said target drive signal being representative of the sustainable respiratory drive target level;
   a signal comparator responsive to the respiratory drive signal and the target drive signal to produce a comparison signal indicative of whether the respiratory drive signal has an amplitude lower or higher than the amplitude of the target drive signal;
   a gain supply responsive to the comparison signal from the signal comparator to supply a gain, said gain supply having a gain-increasing unit which increases the gain when the comparison signal indicates that the amplitude of the respiratory drive signal is higher than the amplitude of the target drive signal, and a gain-decreasing unit which decreases the gain when the comparison signal indicates that the amplitude of the respiratory drive signal is lower than the amplitude of the target drive signal; and
   a gain multiplier responsive to the gain from the gain supply and the respiratory drive signal to multiply said respiratory drive signal by said gain and therefore produce a ventilator control signal for application to and control of the lung ventilator.

2. A lung ventilator control system as recited in claim 1, wherein said target drive signal supply comprises means for producing a target drive signal having an amplitude located within a range of amplitudes.

3. A lung ventilator control system as recited in claim 2, wherein said gain-increasing unit comprises means for increasing the gain by a fraction of a given value, and wherein said gain-decreasing unit comprises means for decreasing the gain by said fraction of the given value.

4. A lung ventilator control system as recited in claim 3, wherein said given value is the target drive signal.

5. A lung ventilator control system as recited in claim 3, wherein said given value is the respiratory drive signal.

6. A lung ventilator control system as recited in claim 3, further comprising means for calculating a difference between the amplitude of said signal representative of respiratory drive signal and the amplitude of said target drive signal, wherein said given value is said difference between the amplitude of said respiratory drive signal and the amplitude of said target drive signal.

7. A lung ventilator control system as recited in claim 2, wherein said muscle of the patient comprises the patient's diaphragm.

8. A lung ventilator control system as recited in claim 1, wherein said detector of the electrical activity of the patient's muscle comprises an array of electrodes.

9. A lung ventilator control system as recited in claim 8, wherein said array of electrodes is a linear array electrodes.

10. A lung ventilator control system as recited in claim 1, comprising means for expressing said respiratory drive signal and said target drive signal as mean signal amplitudes.

11. A lung ventilator control system as recited in claim 1, comprising means for expressing said respiratory drive signal and said target drive signal as median signal amplitudes.

12. A lung ventilator control system as recited in claim 1, comprising means for expressing said respiratory drive signal and said target drive signal as peak signal amplitudes.

13. A lung ventilator control system as recited in claim 1, comprising means for expressing said respiratory drive signal and said target drive signal as total signal amplitudes.

14. A method of controlling a lung ventilator for maintaining at a sustainable target level a respiratory drive of a patient assisted by a lung ventilator during inspiration, comprising:
   detecting the electrical activity of a muscle of the patient indicative of a respiratory drive of said patient, said detecting comprising producing a respiratory drive signal in response to the detected electrical activity;
   producing a target drive signal of given amplitude, said target drive signal being representative of the sustainable respiratory drive target level;
   comparing the respiratory drive signal to the target drive signal to produce a comparison signal indicative of whether the respiratory drive signal has an amplitude lower or higher than the amplitude of the target drive signal;
   supplying a gain, said gain supplying comprising increasing the gain when the comparison signal indicates that the amplitude of the respiratory drive signal is higher than the amplitude of the target drive signal, and decreasing the gain when the comparison signal indicates that the amplitude of the respiratory drive signal is lower than the amplitude of the target drive signal; and
   multiplying the respiratory drive signal by said gain and therefore producing a ventilator control signal for application to and control of the lung ventilator.

15. A method of controlling a lung ventilator as recited in claim 14, wherein producing a target drive signal comprises producing a target drive signal having an amplitude located within a range of amplitudes.

16. A method of controlling a lung ventilator as recited in claim 14, wherein increasing the gain comprises increasing the gain by a fraction of a given value, and wherein decreasing said gain comprises decreasing the gain by said fraction of the given value.

17. A method of controlling a lung ventilator as recited in claim 16, wherein said given value is the target drive signal.

18. A method of controlling a lung ventilator as recited in claim 16, wherein said given value is the respiratory drive signal.

19. A method of controlling a lung ventilator as recited in claim 16, further comprising calculating a difference between the amplitude of said respiratory drive signal and the amplitude of said target drive signal, wherein said given value is said difference between the amplitude of said respiratory drive signal and the amplitude of said target drive signal.

20. A method of controlling a lung ventilator as recited in claim 14, wherein said muscle of the patient comprises the patient's diaphragm.

21. A method of controlling a lung ventilator as recited in claim 14, wherein detecting the electrical activity of the patient's muscle comprises detecting said electrical activity through an array of electrodes.

22. A method of controlling a lung ventilator as recited in claim 21, wherein said array of electrodes is a linear array electrodes.

23. A method of controlling a lung ventilator as recited in claim 14, comprising expressing said respiratory drive signal and said target drive signal as mean signal amplitudes.

24. A method of controlling a lung ventilator as recited in claim 14, comprising expressing said respiratory drive signal and said target drive signal as median signal amplitudes.

25. A method of controlling a lung ventilator as recited in claim 14, comprising expressing said respiratory drive signal and said target drive signal as peak signal amplitudes.

26. A method of controlling a lung ventilator as recited in claim 14, comprising expressing said respiratory drive signal and said target drive signal as total signal amplitudes.

* * * * *